(12) United States Patent
Gimenez Calbo (10) Patent No.: US 9,588,030 B2
(45) Date of Patent: Mar. 7, 2017

(54) DIHEDRAL SENSOR FOR EVALUATING TENSION, POTENTIAL AND ACTIVITY OF LIQUIDS

(75) Inventor: Adonai Gimenez Calbo, Sao Carlos (BR)

(73) Assignee: EMBRAPA-EMPRESA BRASILEIRA DE PESQUISA AGROPECUARIA, Brasilia-DF (BR)

( * ) Notice: Subject to any disclaimer, the term of this patent is extended or adjusted under 35 U.S.C. 154(b) by 714 days.

(21) Appl. No.: 13/520,316

(22) PCT Filed: Jan. 3, 2011

(86) PCT No.: PCT/BR2011/000001
§ 371 (c)(1),
(2), (4) Date: Oct. 25, 2012

(87) PCT Pub. No.: WO2011/079367
PCT Pub. Date: Jul. 7, 2011

(65) Prior Publication Data
US 2013/0145829 A1   Jun. 13, 2013

(30) Foreign Application Priority Data
Jan. 4, 2010 (BR) ...................................... 1000060

(51) Int. Cl.
*G01N 13/02* (2006.01)
*A01G 25/16* (2006.01)
*G01N 33/24* (2006.01)

(52) U.S. Cl.
CPC ........... *G01N 13/02* (2013.01); *A01G 25/167* (2013.01); *G01N 33/246* (2013.01)

(58) Field of Classification Search
USPC .................. 73/64.48–64.52, 64.45, 64.46
See application file for complete search history.

(56) References Cited

U.S. PATENT DOCUMENTS 3,569,722 A * 3/1971 Denson ........................ 356/632
3,797,312 A   3/1974 Campbell
(Continued)

FOREIGN PATENT DOCUMENTS

BR   PI 0004264-1 A   4/2002
BR   PI 0104475-3 A   2/2004
(Continued)

OTHER PUBLICATIONS

"Food Safety Bulletin", BC Centre for Disease Control, http://ucfoodsafety.ucdavis.edu/files/133655.pdf, Mar. 1997.*
(Continued)

*Primary Examiner* — Michael A Lyons
*Assistant Examiner* — Alexander Mercado
(74) *Attorney, Agent, or Firm* — Sughrue Mion, PLLC (57) ABSTRACT

In the dihedral sensor system, two flat plates are secured to a dihedron so that the distance (L) between the edge and the meniscus and the spacing between the plates (a) on the meniscus will be a function of the dihedron tangent ($\alpha$). Thus, for pure water the tension ($\Psi$) is equal to the potential (T) and given by $T=-2\sigma/[L\ tg(\alpha)]$, wherein $\sigma$ is the water surface tension. In order to measure water tension in the soil, the system is coupled to porous elements, while the sensor edge is pressed directly against roots and other plant organs. Water potential, instead, is measured with the edge positioned at a few micrometers from the sample and the response takes place after the exchange of a few picoliters of water, when the condition of balance of temperature and water vapor is approached. Visually, with a sliding gauge, one measures water tensions between zero and 0.3 MPa, while with the aid of a microscope the reading extends up to 3.0 MPa. The water activity corresponding to water potentials lower than −3.0 MPa can also be measured by adding (Continued)

a known number of molecules of solutes suitable for the water kept in the sensor.

14 Claims, 5 Drawing Sheets

(56) References Cited

U.S. PATENT DOCUMENTS

| | | | |
|---|---|---|---|
| 4,523,456 A * | 6/1985 | Baird et al. | 73/64.48 |
| 5,080,484 A * | 1/1992 | Schneider et al. | 356/154 |
| 5,533,393 A | 7/1996 | Bonne et al. | |
| 5,792,941 A * | 8/1998 | Rye et al. | 73/53.01 |
| 5,816,704 A | 10/1998 | Campbell et al. | |
| 5,922,939 A | 7/1999 | Cota | |
| 6,368,664 B1 * | 4/2002 | Veerasamy et al. | 427/249.7 |
| 6,581,438 B1 * | 6/2003 | Hall et al. | 73/53.01 |
| 6,867,854 B1 * | 3/2005 | Wapner et al. | 356/150 |
| 6,926,439 B2 | 8/2005 | Zlochin | |
| 6,982,787 B1 * | 1/2006 | Wapner et al. | 356/138 |
| 8,679,233 B1 * | 3/2014 | Wapner et al. | 95/251 |
| 2004/0145379 A1 * | 7/2004 | Buss | 324/664 |
| 2012/0234357 A1 * | 9/2012 | Labib et al. | 134/22.12 |

FOREIGN PATENT DOCUMENTS

| | | |
|---|---|---|
| CA | 2 404 136 A1 | 9/2001 |
| EP | 1 186 880 A1 | 3/2002 |
| GB | 344341 A | 3/1931 |
| GB | 733602 A | 7/1955 |
| GB | 2 255 190 A | 10/1992 |
| WO | 2005/121781 A1 | 12/2005 |

OTHER PUBLICATIONS

Caciano Zapata Norena et al.; "Técnicas Básicas de Determinação de Atividade de Água: Uma Revisão"; Bol. SBCTA, 30 (1):91-96, Jan./Jun. 1996.

L. A. Richards; "Soil Moisture Tensiometer Materials and Construction"; U.S. Department of Agriculture; Soil Science; vol. 53; pp. 241-248, No. 4, Apr. 1942.

A. M. Ridley et al; "A new instrument for the measurement of soil moisture suction"; 1993 Géotechnique, v. 43, No. 2, pp. 321-324, 1993.

L. A. Richards; "A Pressure-Membrane Extraction Apparatus for Soil Solution"; U.S. Department of Agriculture; Soil Science, vol. 51, pp. 377-386, 1941.

Scholander et al; "Hydrostatic Pressure and Osmotic Potential in Leaves of Mangroves and Some Other Plants"; Proceedings National Academy of Sciences USA (Proc. N.A.S.), vol. 52, pp. 119-125, 1964.

Husken et al; "Pressure Probe Technique for Measuring Water Relations of Cells in Higher Plants"; Plant Physiology, vol. 61, pp. 158-163, 1978.

Bohdan Slavik; "Methods of Studying Plant Water Relations"; Springer, New York, 1974, ISBN 0-387-0686-1; pp. 1-120.

\* cited by examiner

DIHEDRAL SENSOR FOR EVALUATING TENSION, POTENTIAL AND ACTIVITY OF LIQUIDS

CROSS REFERENCE TO RELATED APPLICATION

This application is a National Stage of International Application No. PCT/BR2011/000001, filed on Jan. 3, 2011, which claims priority from Brazilian Patent Application No. PI 1000060-7, filed Jan. 4, 2010, the contents of all of which are incorporated herein by reference in their entirety.

FIELD OF THE INVENTION

A dihedral sensor for measuring water tension and water potential according to the accumulation of liquid between two plates fixed as a dihedron. In principle, the system can be employed for water and other liquids. Upon measuring the water activity or water potential, the systems facilitates the thermal balance required for vapor-pressure balance. Unlike this, in measurements of water tension, the water movement between sample and the dihedral sensor takes place by continuity of the liquid phase through the sensor edge pressed against the sample, for which reason the control over temperature is much less critical in this case. In soils the system should preferably be operated by measuring a porous element that filters and facilitates the conduction of water between the soil and the dihedral sensor. Measurements of water potential and water tensions of up to 3.0 MPa, in the plant, are made under a microscope with micrometry ocular. Measurements of water tensions between zero and 0.3 MPa, in the soil, are made visually with a ruler or a sliding gauge. The qualitative and quantitative applications of the dihedral sensor system embrace applications in handling irrigation in the field and in pots, as well as in physiological studies, and can apply to whole organs or segments.

BACKGROUND OF THE INVENTION

Water activity and water potential are related to each other by equation 1 below:

$$\Psi=(RT/V_w)n(a_w) \quad [1]$$

wherein $\Psi$ is the water potential (Pa), R is the constant of the gases (8.3145 jK$^{-1}$ mol$^{-1}$), T is the Kelvin temperature, $v_w$ (1.8 10$^{-5}$ m$^3$) is the water partial molar volume and $a_w$ is the activity of water, which can be taken as the hundredth part of the relative humidity of balance with the sample.

The evaluation of water activity is very important, for instance, in food technology and in storing grains. For a large number of these products the storage useful life and the quality itself depends on the water activity, which is used as a control parameter.

To the plant physiology and to the handling of water in the soil, however, the notion of water potential with its subdivisions into components, in general, is more used than the notions of relative humidity and of water activity. The water potential was defined as a relationship between the chemical potential and the partial molar volume of water. As a result, the water potential can be treated simply as force per area unit, that is, as pressure. The water potential thus defined is a sum of pressure components. Among these, in the plant, the following are important: the osmotic component (Ws), with which by accumulation of solutes the cell sucks water into itself; the gravitational potential (H), a height to be overcome for water to move between the root in the soil and the leaves and other aerial organs; the turgescence pressure (Ps) inside the cells, a result from the osmotic potential and from the cell membranes and walls; and the water tension in the xylem and in the apoplasma (PA), in the matrix of which the differences in pressure, modulated by growth and transpiration, govern the velocity of transportation fo this fluid between the soil and each organ of the plant.

The term "tensiometer" may be used to designate instrument for measuring the water-tension component either in the soil or in the plant. Various types tensiometer find applications in branches such as plant physiology, handling irrigation and geology. Instruments for measuring water activity, balance relative moisture and water potential (eq. 1) on the other hand could be called preliminarily hygrometers, and they have applications ranging from the purely practical applications to more sophisticated ones directed to science in areas such as plant physiology and food technology.

Much of the classic technology on construction and uses of tensiometers and hygrometers for studying echophysiology of plants were revised by Slavick (Methods of studying plant water relations, Springer, New York, Springer, 1974, ISBN 0-387-06686-1), and with regard to the water activity in foodstuffs, several frequently used methods are briefly described by Zapata et al. (Bol. SBCTA, v30, n. 1, pp 91-96, 1996).

The ordinary tensiometer (Soil Science, v. 53, pp 241-148, 1942), used for handling irrigation, is constituted by a porous capsule with a cavity filled with water, hermetically connected to a vacuum gauge. Its working ranges from zero pressure to barometric pressure, but in practice it is used mainly between zero and 70 kPa. The most widespread use of the ordinary tensiometer is as a reference instrument in handling irrigation. The great limitation of the ordinary tensiometer, in turn, is the occurrence of embolism, that is, accumulation of air in water contained in the cavity of the porous capsule. This gradual accumulation of air causes the tensiometer to lose response velocity and to undergo a related reduction of the maximum working tension, while the accumulated volume of air increases in the sensor cavity. The maintenance required for the tensiometer to function again is opening the lid, adding water, closing it and await a new response of dynamic balance. This seems to be easy maintenance, but this work has been the great obstacle for the ordinary tensiometer to be used in automation, in the face of the demand for sensors that operate with low or no maintenance.

Module water tension higher than barometric pressure, which rises up to 1500 kPa or higher, can be measured with the tensiometer developed by Ridley & Burland 1993 (Géotechnique, v. 43, pp 321-324, 1993). The principle of this high-performance tensiometer is similar to that of the ordinary tensiometer, from which it differs in that it has a cavity with a reduced volume over a porous element of high bubbling pressure, an electronic pressure transducer and in that it is pre-hydrated to over 4000 kPa for at least 24 hours, in a hyperbaric chamber, in order to dissolve the air bubbles. It is a high-performance instrument in the sense of high water pressures which it measures. However, it is an instable instrument, the operation of which is often interrupted by the occurrence of embolism, after at most a few hours of operation. Embolism in this instrument has a much more devastating and instantaneous effect than that experienced with an ordinary instrument, when the water tensions measured are much higher than the barometric pressure module. In spite of this limitation, this is a valuable system for geophysicists and engineers who need to measure mechanical properties of soils in a wide range of water tensions.

A system of measuring water tension that does not have the embolism limitation is that described in document BR PI 0004264-1. In this system, porous capsules with the cavity filled with air and without water are subjected to air pressure so that the water tension will be measured by difference between the parameter pB (bubbling pressure) and air pressure (p) required to force permeation of the gas through the wall of the porous element. Porous elements with properties suitable for different agricultural applications and different instruments of system use are available commercially.

Most instruments for measuring water tension in the soil are gauged in a pressure chamber with porous membrane or disc, the called Richards chamber (Soil Science, v. 51, pp 377-386, 1941). In this pressure chamber, water is forced out of the equipment through the porous membrane on which the study sample rests, usually the soil. The time of balance of water tension depends on factors, among which are important the thickness of the soil layer and the bubbling pressure of the membrane. The water tension in the balance is equal to the air pressure applied. This instrument has been used mainly to establish curves between the moisture and the water tension in the soil, the so-called retention curves and volume-pressure curves. However, this is a gauging device, not a water-tension sensor proper. As a limitation, the adjustment of high tensions is too slow, because the hydraulic conductivity of the soil decreases exponentially with the water tension.

For preserving grains and various food products, it is indispensable to maintain the water activity that corresponds to matrix potential and total water potentials much higher than 3.0 MPa ($a_w$>0.98). For instance, grains in hygroscopic balance with relative humidity of 50% would have $a_w$=0.50 and water potential of 96 MPa. For gauging these instruments, which measure water activity, techniques of hygroscopic balance with saline solutions and instruments for preparation of reference relative humidity are used. A simple system that makes use of hygroscopic salts for adjusting relative humidity in chamber under controlled temperature was invented by Greaves in 1991 and is described in document GB 2255190. Other international systems accepted for gauging hygrometers are: 1) gaseous mixtures of air from two pressures, one of saturation and the other of measurement, both in isothermal environment; 2) mixtures of air from two temperatures, one of saturation, more reduced, and the other of higher measurement; 3) and the gravimetric system in which a known mass of water is vaporized inside a container of known volume and finely adjusted temperature (PI BR 0104475-3).

Water activity or relative humidity of balance is the main variable related to the preservation of foods (Bol. SBCTA, v. 30, pp 91-96, 1996). The methods for determining water activity in foods are varied and include:

a) Gravimetric methods, which are based on determining the drying (desorption) or moistening (sorption or adsorption) curve of a food or soil during the balance with reference saturated saline solutions in isothermal condition. This is a method the velocity of which decreases rapidly as a result of the increase in the dimensions of the organs, or sample units, and it may take weeks or even months depending on the material. It is a method that needs to be applied at strictly controlled temperature in order to prevent water condensation. In addition, the saturated solutions employed should preferably adjust the water activity in a manner practically independent of temperature, that is, with a small thermal coefficient. Since this method involves a long wait, it can only be used for little perishable foods, as is the case of various seeds.

b) An isopiestic procedure involves strips of filter paper soaked in different saturated reference saline solutions. These strips are weight and placed into the chambers with the product for 24 to 48 hours. Each strip may gain or lose mass depending on whether its water activity is higher or lower than the water activity of the sample. Thus, by using graphic interpolation, one estimates the water activity of the sample in which the strip soaked in an adequate saline solution would not undergo variation in mass. It is a method of good quality and low cost, but it is a procedure that involves "attempts" and is considered a slow method.

c) The balance method with a sensor of an reference absorbent material made of cellulose or casein, for example, involves the preliminary establishment of a calibration curve that relates the sensor mass and the water activity from standardized saline solutions. Then, the sensor of absorbent material is put together with the sample and, after a period of 24 to 48 hours, one determines its final balance mass, taking care to prevent any loss of water until the weighing. The water activity is then calculated in accordance with the sensor mass, by using the calibration curve. This technique functions for desserts and could be used for plant organs with water activity ranging from 0.8 to 0.99. This is a low-cost and interesting method with precision on the order of 0.002 units of water activity. It is also a slow method whose response stability depends on the absorbent material. An important limitation of this technology is that it is not suitable for water potentials close to zero.

d) Fiber hygrometers for measuring relative humidity, as described in document GB 344341 of 1931 are simple and practical. These instruments, however, require frequent calibration, since fibers like those of degreased hair thread, for example, lose their elasticity as time passes. Moreover, they are instruments that have not been built specifically for measuring water activity in foodstuffs.

e) Resistive electronic hygrometers that, in general, are made from a blade of an invert material, coated with a hygroscopic layer of lithium chloride, for example. In these systems the electric conductance varies as a function of the relative humidity of air. The precision of this type of device is on the order of 0.005 unites of $a_w$. Bonne et al, in 1996, developed a stabilized rapid-response microsensor for measurement of absolute units and of dew-point temperature based on the hygroscopicity of lithium chloride, according to description in document U.S. Pat. No. 5,533,393. The present degree of sophistication of these resistance devises may be high, as can be observed in the resistive sensor with a porous element and heating, described in document Speldrich WO2005/121781, in which the electronic heating of the porous element vaporizes condensed water droplets and also enables the determination of relative humidity higher than 100%. The response of the electrical resistance devices, however, tends deteriorate, for instance, by dilution or by accumulation of ions on the inert matrix.

f) A second category of electronic hygrometers are those of capacitance, which make use of the high dielectric constant of water vapor, in comparison with air. One of these systems with aggregation of complexity for improvement of the precision is described in document U.S. Pat. No. 5,922,939. In general, these are absolute-humidity sensors that respond rapidly and that require thermal corrections for measurement of relative humidity. Additionally, they tend to be little sensitive in measurements of relative humidity close to saturation. Capacitive sensors, just as resistive sensors, in general, require frequent calibration.

g) Dew-point temperature method for measuring the water activity, in general, requires measurement of temperature over a thermocouple surface or a cooled mirror surface, for example. The dew-point systems can also produce wrong estimates of the water activity, if the cooled surface is contaminated by impurities, and also in the case presence of volatile substances. In general, the instruments based on dew-point temperature are more stable and less subject to interference than electrical resistance hygrometers and those of capacitance.

h) In the psychometric method the temperature of a thermometer with humid bulb and the temperature of the dry-bulb thermometer, of reference, are used to estimate the water activity. Usually, the humid bulb is humidified thanks to the previous condensation of water onto a cooled surface by application of electric current (Peltier effect).

Among the instruments for measuring water activity, those that have been considered the best ones are those that use the dew-point method, according to the temperature at which the condensation of water on a clean and hydrophilic surface is started. Campbell, in 1974, developed a hygrometer based on thermocouples and the Pelier effect for measuring osmolality, water activity, or water potential of solutions and plant samples. The device, the electronics and the methodology for using the instrument at the drew point and in the psychometer mode of humid bulb are described in document U.S. Pat. No. 3,797,312. One of the qualities of the equipment described is the portability and the fact that it does not require a sophisticated thermal bath system for measuring water activity in small samples of plant and of solution. In the psychometric mode the temperature of the humid bulb formed after condensation of water and the temperature of the dry bulb of reference are used for estimating water activity. Other devices that use the dew-point method make use of a mirror as in the case of the device of Zlochin (2005), described in document U.S. Pat. No. 6,926,439, in which the mirror always free from impurities brought by air is used for application of the dew-point method. Zlochin argues that one of the great problems of the dew-point method is the accumulation of impurities carried by air. The removal of these impurities is difficult, because there is a demand for frequent cleaning the cooled surface, so that the quality of the measurements will not be impaired.

According to Campbell & Lews (1998), in the system for measuring water activity by the dew-point method of document U.S. Pat. No. 5,816,704, and in other devices that make use of this principle, the error in estimating the dew-point temperature is given by the equation: $Erro^2 = 2\ r\ a\ w/s$, wherein r is the resistance of the laminar layer ($s\ m^{-1}$), w is the inclination between the saturation vapor pressure and the temperature, w is the condensation rate in $g\ m^{-2}\ s^{-1}$, and s is the concentration of saturation vapor in $g\ m^{-3}$. From this equation it becomes evident that methods that decrease the laminar layer and the amounts of condensed water for the measurement also diminishes the error in estimating the dew-point temperature and increase the response velocity of the instrument.

Unlike the case of soils, considered initially, the development of devices for measuring water tension in plants has been more rare, in spite of being a fundamental variable to explain the rising of the sap. In the prior art the most widely used method for measuring water tension in plants have been the Scholander pressure chamber (Proceedings National Academy of Sciences USA, v. 52, p. 119-125, 1964). For use, a leaf, for example, is secured to the orifice of the sealing rubber, so that the petiole can go through the cover that closes the chamber hermetically. Upon measuring, the gas pressure in the chamber increases slowly until the first sap drop pours through the petiole. The gas pressure applied, in this condition, is then taken as stimulative of the water tension in the leaf. In the current literature, however, there are controversial positions on the validity of this method, the weak point of which is that it does not have a gauging form. In spite of this, and even involving destructive samplings, the Scholander pressure chamber is the most widely used instrument for studying water relations in plants.

The water tension in a plant has also been measured by inserting a capillary tube into the xylem pots (Plant Physiology, v. 61, pp 158-163, 1978). However, this method, called pressure probe method, is extremely difficult, laboratorial and has not enabled measurements of tensions higher than 800 kPa in a plant. In the comparative measurements of water tension in plants by using the pressure probe and the Scholander pressure chamber, additionally the results have not always been equivalent, within the margins of error.

In the present invention, one describes a simple method for measuring water potential, water tension and water activity, which can be gauged through calibration by different procedures. In measurements of water tension, the system of this invention is not subject to embolism problems, a typical problem of a tensiometer. In order to measure water potential, the system may present a rapid thermal balance, using a contact microchamber. In measurements of water tension in the soil, it enables readings by simply using a sliding gauge in the range from 0 to 0.3 MPa. The water potential may be measured with a microscope between zero and 3.0 MPa. In plants, additionally, under a microscope, the water tension measured by putting the sensor against the sample by flattening, is on the same order as the measurement of water potential.

SUMMARY OF THE INVENTION

The dihedron plate system of this invention enables linear measurements of water tension, when the transport between the dihedron and the sample takes place through the liquid phase, and equally linear measurements of water potential in this system are carried out by using water transport between the sample and the dihedron sensor by means of the gaseous phase. In order to measure water potential, the dihedron edge is positioned at a few micrometers from the sample. In the dihedron, the angle is such, that an evaporation of few picoliters can be detected, as movement of the meniscus. In this way, the water balance with the sample, in general, is detected in a few minutes. In measurements of water tension in the soil, the water volumes exchanged by the dihedron are much larger, on the order of microliters, in order to enable visual evaluations with a sliding gauge. For soils, the plates are secured onto appropriate porous elements. The porous element may be of surface or of insertion in a defined depth. The outer face of one of the plates may be painted black in order to facilitate distinction of the meniscus that separates the darker stripe filled with water at the side of the edge and the clearer range stripe filled with air and away from the edge. In measurements, the distance L taken between the edge and the meniscus multiplied by the dihedron tangent angle (α) is equal to the spacing a between the plates. In this way, if the dihedron contains pure water, then the water tension (Ψ) and water potential (T) are equal and are given by the equation: $\Psi=T=-2\ \sigma/[L\ tg(\alpha)]$, wherein σ is the surface tension of water in $Nm^{-1}$. In readings with a sliding gauge, one measures water tensions from zero to 0.3 MPa, while in readings under a microscope one measures water tensions and water potentials from zero to 3.0 MPa.

DETAILED DESCRIPTION OF THE INVENTION

In the present invention a system of plane and hydrophilic plates, made of glass or a finely porous material, secured to dihedron (FIGS. 1; 1 and 2) is used to measure water tension and other components of water potential in soil, plant and foodstuffs. This dihedron sensor illustrated herein in its simplest form (FIG. 1) enables measurements of water tension, water potential and water activity according to the position of the meniscus (4), in balance condition. The material of the plates, the reading accessories, the measurement range, the possibility of an external hydrophobic coating and the sizing of the dihedron sensor are defined in accordance with the purpose of use.

Figure 1:
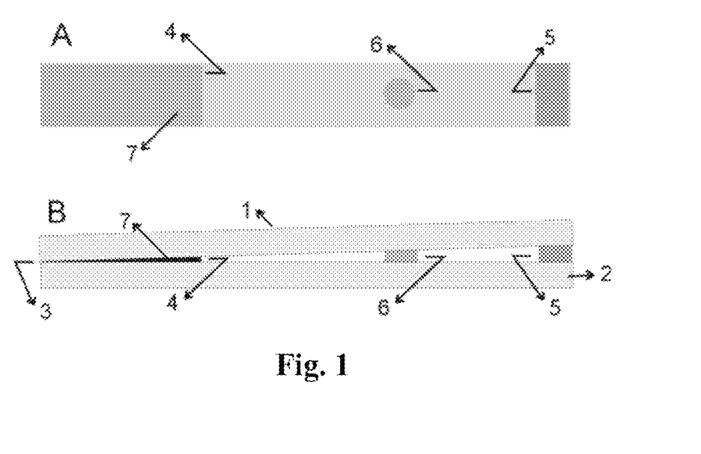
FIG. 1 is an illustration of the dihedron sensor made of hydrophilic glass plates for measuring water tension according to the distance between the vertex and the meniscus; A—front view; B=top view
Figure 2:
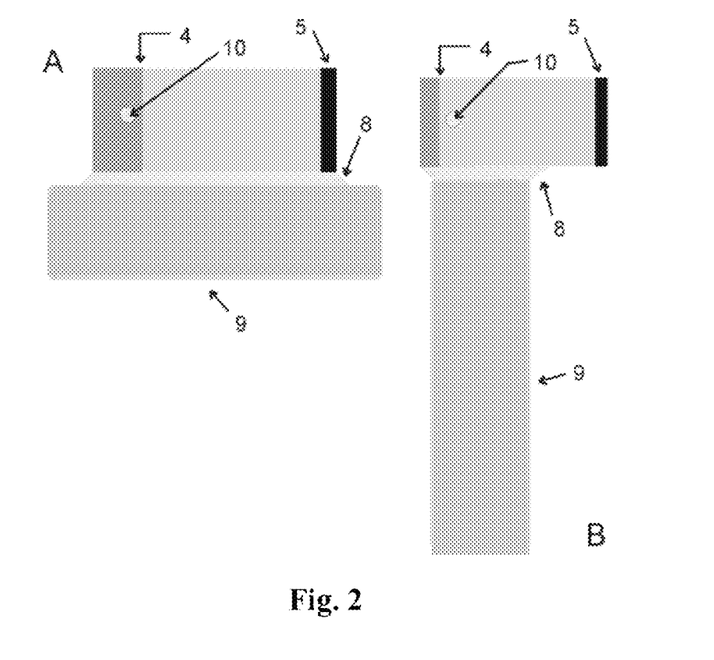
FIG. 2 shows a dihedron sensor made of transparent hydrophilic glass plates for measuring water tension in soil, containing porous elements coupled by permeable cement; A—porous element in disc for surface measurement; B—elongate porous element for insertion into the soil.

According to FIG. 1, from the dihedron plates (1, 2) at least the upper plate (1) should preferably be transparent in order to facilitate viewing of the water (7) and the position of the meniscus (4). In order to understand the different uses, the lower plate (2), on the other hand, may be transparent, black, mirror-like or microporous.

The measurement of water tension in the soil should preferably be made with the dihedron system secured onto the porous elements (9), as shown in FIG. 2. In this case, the dihedron sensor is secured to the porous element (9) with porous cement (8). If the dihedron sensor is secured to the disc of the porous element (9), it will be ideal for measuring water tension of the surface of the soil of plant pots (FIG. 2A). On the other hand, in order to measure water tension in specified depths, the dihedron sensor needs to be secured onto the elongate porous element (9), as shown in FIG. 2B, the side walls of which may be made impermeable as far as the desired reading depth. The porous element should have porosity and bubbling pressure, or critical working tension suitable for the operation range considered for the sensor.

Figure 3:
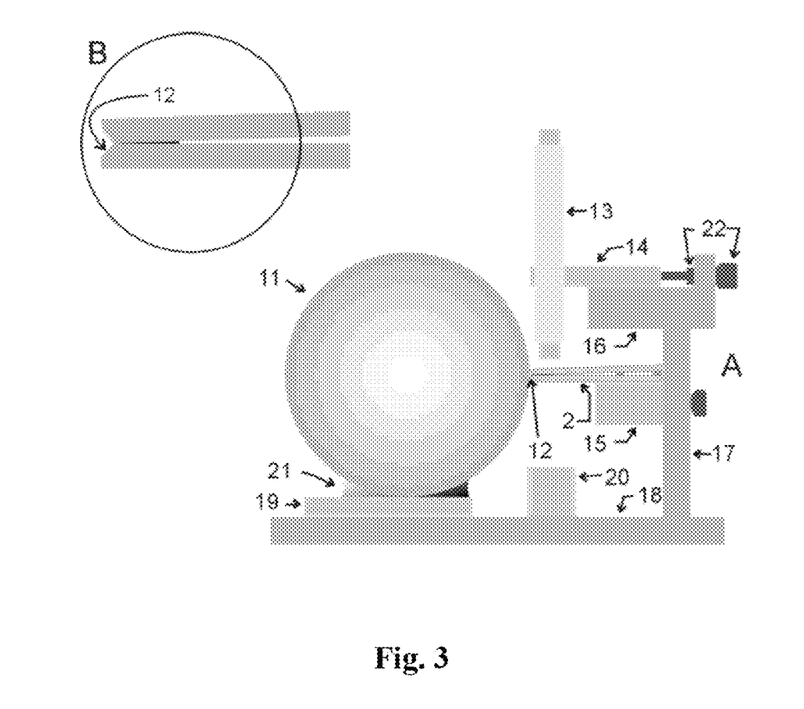
FIG. 3 is a dihedron sensor in microscope with microchamber for balance of water-vapor pressure to facilitate the positioning and rapid balance of water-vapor pressure required in measurements of water potential and water activity.

For measurements of water tension and water potential in plants, the dihedron sensor should be used with the aid of a microscope (13) (FIG. 3A). To this purpose, the dihedron is supported on a block (15) for manipulation. In the simple arrangement of the illustration, the product onto a parallelepiped (19) and the source of light (20) onto a plane base are moved by sliding on the slide base (18). In order to measure of water tension, the "edge" of the dihedron sensor is pressed against plant samples of high hydraulic conductivity, roots, for example, so that the water tension in the plant will govern the water tension in the dihedron sensor by transporting water directly in phase. In this application, the dihedral sensor enables measurements of water tension in the plant in a manner that has not yet been effected by previous system. The reading of water potential requires a slightly different procedure, in which the edge is approximated up to a few micrometers, without, however, resting against the sample. In this system the exchange of water through the edge between the sample and the sensor takes place through gaseous phase. This exchange of water in the gas phase should occur through a very fine layer of stagnated air of a few micrometers, in which the thermal and hygroscopic balanced conditions are achieved rapidly. In the measurements of water potential, the use of a dihedron sensor of cut and polished glass, which forms a microchamber (12) (FIG. 3b) pressed against the plant organ (11) is very useful. The microchamber is formed by joining glass plates with frontal polishing, which facilitates the balance of temperature and water-vapor pressure required for measuring water activity. In this microchamber, the edge (3), from where the exchange of water takes place, in gaseous phase, is in a condition favorable to the rapid heat and water balance, even without resourcing to a sophisticated thermal control. The polished plate also facilitates the application of a hydrophobic coating to the sides of the dihedral sensor, by friction, for instance. This hydrophobic application is valuable, for instance, for preventing the water from leaking through the glass surface, which tends to delay the response of the system.

Manipulation and Microscopy

The accessory of auxiliary manipulation of the illustration (FIG. 3) may have a polyacetal body with slide base (18), vertical support (17) and upper support or stage (16). For manipulation, the biological sample (root, for example) is placed on parallelepipeds of adequate height (19), with the aid of a plastic mass (21). The parallelepiped (19) is preferably constituted of plastics such as polyacetal to facilitate the smooth sliding over the base (18), even without using lubricant. In the vertical, a block (15) of polyacetal is moved as far as the adequate height and the position is then fixed by screwing.

The source of light (20) is positioned by sliding beneath the dihedron, so that the water/air meniscus (4) will be observed by transparency under a microscope (13). The microscope (13), on the other hand, is moved vertically on thread or rack for focusing. The horizontal movement of the microscope to facilitate the viewing and the measurement of the distance L between the meniscus (4) and the edge (3) takes place according to micrometric set (22) that moves the microscope support (14) on the stage (16). The microscope ocular for these measurements should preferably be micrometric.

Fixation of the Plates

FIG. 1 illustrates the dihedron plates secured with glue (6). For this assembly the back spacer (5) of known thickness is placed over the plate 2. Very small portions of glue are applied with a needle tip. The plate 1 is positioned and ultraviolet radiation is applied for hardening the glue.

When used in soils and substrates (FIG. 2), the plates of dihedron and porous element (9) are joined by porous cement (8) with the following procedures: the plates 1 and 2 are secured to the back spacer (5) preliminarily along the length, with the aid of adhesive tape. The assembly is then laid with cement and water mass over the porous element (9) previously wetted. The porous cement layer (8) between the glass plates and the porous element (9) should be very thin. The curing of the cement takes place on a tray with a layer of water on the bottom, for a period of a few days. After curing, the tape for preliminary fixation of the glass plates is removed, and the outer surface of the dihedron sensor is carefully washed, to remove from the glass cement and adhesive-tape particles adhered to it.

Figure 4:
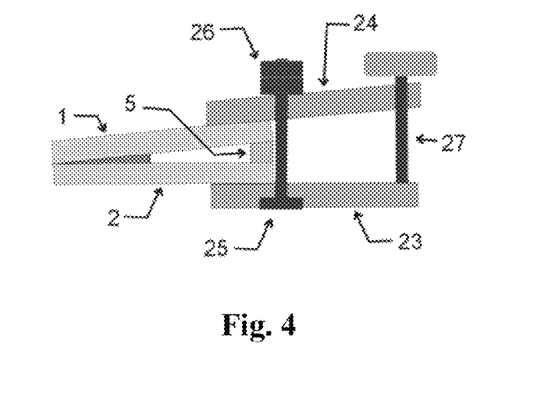
FIG. 4: shows a dihedron sensor with moveable plates to enable cleaning.

In uses in which the possibility of cleaning the inner faces of the dihedral sensor, the system may be assembled as shown in FIG. 4. In this case, the glass plates (1, 2) of the dihedron are glued to plates of greater flexibility (23, 24), for example, "hard" PVC. On plate 23 one secures a guide screw (25), the rod of which rises from a bore close to the glass plate (2). The upper flexible plate (24) receives a bore for free passage of the guide screw (25) close to the upper glass plate (1). Additionally, the upper flexible plate (24), at the back, receives a threaded bore, in which the movement screw (27) of the glass plates turns. In this system, the back spacer (5) also serves to position the screws that compose the height limiter (26).

Figure 5:
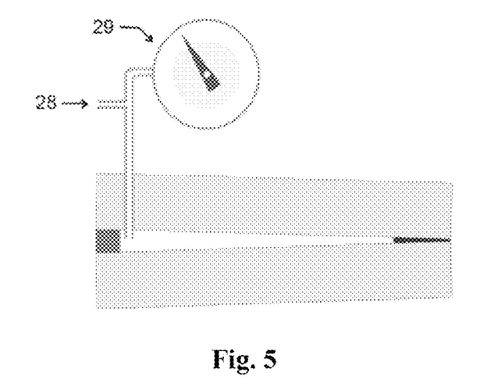
FIG. 5 shows a dihedron whose sides are sealed to measure water tension by applying air pressure between the plates.

For direct gauging evaluations of the system with compressed air and also for the dihedral sensor to function in the tensiometry mode, the system assembly may be of the type illustrated in FIG. 5. In this format, the sides of the glass plates are glued with high viscosity resin, which does not penetrate between the plates 1 and 2 during the cure. A perforation in the glass plate (2) is used as entrance for the air-pressure adjustment tube (28), which is also connected to a manometer (29). The water tension in this case is given by the equation 2:

$$T = Tr - p \quad [2]$$

wherein Tr is the air pressure to adjust the meniscus in the reference position, when the edge is exposed to free water, p is the air pressure required for the measurement and T is the estimated water tension of the sample.

Figure 6:
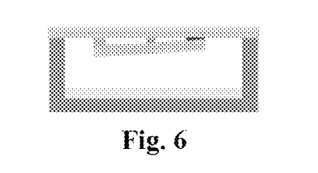
FIG. 6 shows a dihedron sensor inside a hygroscopic balance chamber during measurements of water potential of fluids like fruit homogenates and jellies.

Another way to prepare a dihedron is the arrangement under a glass cover, as shown in FIG. 6. This type of assembly of the dihedral sensor is valuable for measuring water activity in biologic fluids, sweets and homogenates of plant and animal tissues. However, the measurement with this type of system is lower and requires good isothermal bath.

Water Tension

The tension T with which water is retained between the plates of the dihedral sensor can be calculated with this expression:

$$T = -2\,\sigma/a \quad [3],$$

wherein $\sigma$ is the water surface tension at the temperature of the assay and a is the spacing between the plates (1, 2) in the meniscus line (4), expressed in meters. When the wetting angle ($\square$) on the plate is higher than zero, then the equation 3 should be corrected by multiplying the T obtained, in equation 3, by [cos $\square$]. In the applications considered herein for highly hydrophilic glass and ceramic plates, the value of [cos $\square$] will be considered equal to 1.00. Additionally, for applications in irrigation handling under low water tensions a correction for capillary ascension in the porous element (9) may also become necessary.

The equation 3 may be modified so as to represent the spacing a as a function of the distance from the meniscus line to the edge L (in meters), knowing that a=L (tgα). By replacing this value of a in the equation 3, one obtains:

$$T = -2\sigma/[L(tg\alpha)] \quad [4].$$

In a system with plates of 60 mm in length and 30 mm in width, encountered at the edge and separated by 50 μm on the back spacer (5) secured 50 mm from the edge (3), one calculates that, each millimeter of distance L, the spacing a between the plates increases by 1 μm. If L is 30 mm broad, and considering that the water surface tension (σ) at 20° C. is 0.0728 N m−1, then the water tension in the soil balanced with the sensor, calculated with the relationship T=−2 σ/a, is of 4853 Pa, or 4.85 kPa. The system of plates in dihedron configured as shown in FIG. 2 is suitable for use with substrates and enables measurements of water tensions between 2.91 kPa and 29.1 kPa, while the meniscus position changes from a distance L1=50 mm in pot substrate with water tension of 2.91 kPa to L2=5 mm in drier substrate, in which the water tension has already reached 29.1 kPa. Evidently, this sensor also enables one to measure higher water tensions, but for this purpose the use of a amplifying glass is required.

For field studies, in which there is interest in measuring higher water tensions, the spacer (5) could be of lower thickness, for example of 10 μm. In this way, each millimeter of horizontal distance (FIG. 1), the spacing a between the plates would increase by only 0.2 μm. With this specification, the system of plates in dihedron is suitable for measuring water tensions five times higher than the previous one, that is, it enables measurements of water tension ranging from 14.6 kPa and 145.6 kPa, while the distance L of the meniscus during the drying is reduced from 50 mm to 5 mm, according to equations 1 and 4.

Dihedral sensors coupled to porous elements (9) as shown in FIG. 2, as well as ordinary tensiometers, require height corrections, in view of the hydraulic communication between the dihedral sensor on which the hydraulic conduction porous element (9) opens for contact with the soil. This need becomes more important when the tensions that should be maintained in the substrates decrease, as happens, for instance, in handling irrigation of plants in pots.

Sensor on Porous Element

Direct contact of the dihedral sensor with the soil or the plant may introduce particles, the accumulation of which between the plates impairs the response. In order to reduce this problem and to ensure an effective hydraulic coupling between the soil and the dihedral sensor, the dihedron may be secured to the porous element (9) by means of porous cement (8). The porous element (9) filters the water while the porous cement (8) is the hydraulic coupling. From the geometrical point of view, the porous element may be a ceramic disc, when the sensor is prepared to rest over the substrate, ion a plant pot, for example, or be a cylindrical rod when this dihedral sensor needs to be inserted into the soil for evaluation of water tension in a greater depth.

Plant pots, in general, have little depth and so they should be filled with coarse-texture substrates. In coarse-texture substrates, after watering, the larger pores remain filled with air, unlike fine-texture substrates which, in pots, are completely filled with water. The air between the substrate or soil particles is fundamental for oxygen to go on feeding the cells, so that the roots can breathe. In this way, in substrates of pots and sandy soils, which retain water weakly, the critical tension at which irrigation should be applied is low, usually lower than 10 kPa. If one waits for the substrate to dry more than that, then in this big-particle substrates the plants will not have sufficient amounts of water to absorb anymore. Therefore, in applications of this type the dihedral sensor, in the specification considered, will indicate that the irrigation should be applied as soon at the dart stripe, which corresponds to the distance L, becomes lower than 14 mm.

For measuring water tension in specified depths, for example 20 cm, the porous element (9) in the form of elongate rod should be coated with paint or insulating tape as far as the depth mentioned, in order ensure that water exchange with the soil will take place in the depth or in the depth range of interest.

With the porous element (9), the total variation of the water volume involved in a measurement is the variation of the water contained in the dihedral sensor, plus the variation of the water amount contained in the porous element (9). For high water tensions, in cases where the hydraulic conductivity in the porous element not depends on the water tension, the variation of the water volume in the porous element is given by the product of the water compressibility by the variation of water tension. This approximation is valuable for rapid achievement of half-response time estimates for the system. From the practical point of view, however, measurements of water tension in handling irrigation with a dihedral sensor are greatly facilitated by the fact that types of response on the order of hours are sufficient and easily obtained.

Alternative Readings

With the introduction of an air tube (28) through the plate (2) and hermetical lateral closing of the dihedral sensor (FIG. 5), one can measure water tension by using the equation 2. However, the use of the relation $T=Tr-p$ (Eq. 2) for the dihedral sensor, is different from that described in document BR PI 0004264-1, since in the dihedral sensor the measurement is made without passage of air, while in document BR PI 0004264-1 the measurement is made by permeation of a porous element with air. Another interesting feature regarding this system with hermetic lateral closing (FIG. 5) is its potential for use as an instrument for measuring surface tension, not only of water, but also of any other liquid.

Additionally, the dihedral sensor can function as if it were a porous element for measurement of water tension as taught in document BR PI 0004264-1. However, for this purpose the plate of FIG. 5 should receive one more bore, in this case a vent bore (10) arranged at a distance L from the edge. Still in this application, the dihedron system of the present invention differs from BR PI 0004264-1 in that one can define the critical tension Tr or pB by simply locating the air vent (10).

A more sophisticated form of locating the meniscus position with the use of optical interference, for example, may also prove to be valuable in measurements of high water tensions, in which the spacing a is on the order of a wavelength of visible light (400 to 700 nm).

Calibration of Water Tension

Figure 9:
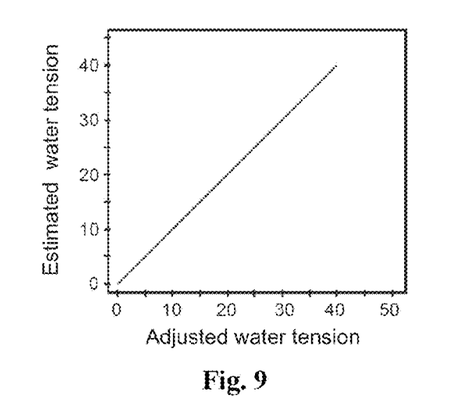
FIG. 9 shows a curve between water tension adjusted in a Richards chamber of negative pressure and reading of the dihedron sensor.

The responses expected at 20° for water tension, volumes of water and distance L of a dihedral sensor with $tg(a)=0.001$ are illustrated in Table 1. These responses in soils and substrates may be compared, assessed, with the aid of a Richards negative-pressure chamger. In this method, one adjusts the water tension to a fine layer of soil and assesses the reading obtained in the dihedral sensor against this reference method, as shown in FIG. 9.

TABLE 1

Spacing between plates (a), water tension T, meniscus distance to edge L, water volume contained between the plants considering that the dihedral angle has $tg(\alpha)$ equal to 0.001 and balance water activity. For assay at 20° C., wherein $\sigma = 0.0728 N\ m^{-1}$.

| a µm | T in meters of water column | T Pa | L mm | Volume in nanoliters per cm of length | $a_w$ |
|---|---|---|---|---|---|
| 2000 | 0.0074 | 72.8 | 2000 | 20000000 | 0.9999994 |
| 200 | 0.074 | 728 | 200 | 200000 | 0.9999946 |
| 20 | 0.742 | 7280 | 20.0 | 2000 | 0.9999462 |
| 18 | 0.825 | 8089 | 18.0 | 1620 | 0.9999402 |
| 16 | 0.928 | 9100 | 16.0 | 1280 | 0.9999328 |
| 11 | 1.061 | 10400 | 14.0 | 980 | 0.9999231 |
| 12 | 1.238 | 12133 | 12.0 | 720 | 0.9999104 |
| 10 | 1.485 | 14560 | 10.0 | 50 | 0.9998925 |
| 8 | 1.856 | 18200 | 8.0 | 320 | 0.9998656 |
| 6 | 2.48 | 24267 | 6.0 | 180 | 0.9998208 |
| 4 | 3.71 | 36400 | 4.00 | 80 | 0.9997312 |
| 2 | 7.43 | 72800 | 2.00 | 20.0 | 0.9994625 |
| 1 | 14.9 | 145600 | 1.00 | 5.0 | 0.9989252 |

TABLE 1-continued

Spacing between plates (a), water tension T, meniscus distance to edge L, water volume contained between the plants considering that the dihedral angle has tg(α) equal to 0.001 and balance water activity. For assay at 20° C., wherein $\sigma$ = 0.0728N m$^{-1}$.

| a µm | T in meters of water column | T Pa | L mm | Volume in nanoliters per cm of length | $a_w$ |
|---|---|---|---|---|---|
| .8 | 18.6 | 182000 | 0.80 | 3.2 | 0.9986568 |
| .6 | 24.8 | 242667 | 0.60 | 1.80 | 0.9982095 |
| .40 | 37.1 | 364000 | 0.40 | 0.80 | 0.9973154 |
| .20 | 74.3 | 728000 | 0.20 | 0.20 | 0.9946380 |
| .10 | 148.5 | 1456000 | 0.10 | 0.050 | 0.9893048 |
| .05 | 297 | 2912000 | 0.05 | 0.0125 | 0.9787239 |
| .03 | 495 | 4853334 | 0.03 | 0.0045 | 0.964792 |
| .02 | 742 | 7280000 | 0.02 | 0.0020 | 0.9476556 |
| .01 | 1485 | 14560000 | 0.01 | 0.00050 | 0.8980511 |

For water tensions higher than the local barometric pressure module, the assessment may be made in an ordinary Richards chamber, that is, positive-pressure Richards chamber. In this case, depending on the membrane used, a rebound error may occur, as soon as the pressure applied in the Richards chamber returns to zero. This problem may be diminished by using a thicker layer of soil, so that no significant rebound will occur, in the period between the opening of the Richards chamber and the balanced reading of the dihedral sensor on the soil surface inside it.

Limitations in Measurements of Water Tension

The functioning of the dihedral sensor (Eq. 3 and 4) depends on the water surface tension (σ), while σ decreases linearly as a function of the temperature. In this way, if one knows that the water surface tension is of 0.0756 N m$^{-1}$ at 0° C. and that it decreases to 0.0696 N m$^{-1}$ at 40° C., then one can calculate the its value at any temperature until the surface tension becomes null. The minor variation in the water surface tension ranging from 0 to 40° C. is a favorable feature, since for applications of lower pressure one, in general, can consider the environment as being isothermal, even if variations in temperature on the order of 5 or 10° C. occur.

The water surface tension, additionally, is influenced by surfactants just as detergents, urea and some pollutants are, which cause reading errors for this instrument in applications on soils and polluted substrates. Salts used as manure, on the other hand, have an almost negligible effect on the water surface tension and are not important causes of errors.

In irrigation handling, the variations in water surface tension, from the point of view of a water retention curve, are automatically corrected, since the effects of surfactants, of temperature and of water surface tension are always proportional to the effects of these factors on the capability of the soil or substrate to retain water. Thus, the possible addition of fertilizers, especially adhesive and other substances, with surfactant action that reduces the force of retaining water in the soil or substrate will also have a proportional effect on the reading of the dihedral sensor. As a result, the parameter L is a more robust index than water tension itself to represent adequately the amount of water retained in the soil. From the point of view of restoration of the instrument response, on the other hand, it is known that a mere cleaning restores, even if transiently, the correct water-tension response, in these polluted systems.

Solutions and Water Activity

Figure 7:
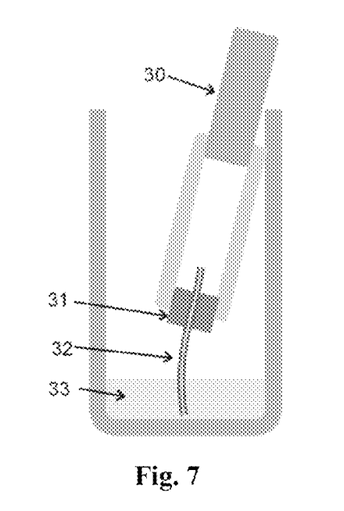
FIG. 7 shows a system for application of known volumes of solution to the dihedron sensor.

The solution applicator of FIG. 7) enables the collection of very small known volumes of solutions to the dihedral sensor. The solution applicator functions as follows: one places the applicator tip (32) in the solution (33); the filling of the capillary tube of the application secured on a cork (31) is spontaneous, that is, by capillarity. The application of the solution is made after, at the designated spot, by pressing the piston (30).

The volume of solution collected may be directly applied onto the edge, in the case of use of polished plates (12) (FIG. 3B), which preferably should have their outer surface covered by hydrophobic substance. Alternatively, the plates may contain a bore, or cut-out at an angle close to the edge to facilitate penetration of the solution. Also, the use of the dihedron opening system shown in FIG. 4 can be interesting, in which the plates are separated for application of the solution.

Having introduced a volume of solution, one knows also that the osmotic potential ($\Psi_s$) is given by:

$$\Psi_s = -nRT/V = RTC_0 \quad [5],$$

wherein V is the volume of water contained between the plates and n is the number of molecules dissolved in the water in moles and $C_0$ is the molar concentration of the added solution. The volume of water V contained in the dihedron, by cm of width, on the other hand, can be expressed by:

$$V = 0.005 L^2 tg\, \alpha \quad [6],$$

wherein L is the distance from the meniscus to the edge and α is the angle between the dihedron plates, or merely dihedron. If the water tension component can be disregarded as very small on the dihedral sensor, then the total water potential Ψ will depend only upon the osmotic potential (eq. 5). Thus, by dividing the expression that represents Ψ by the expression that represents $\Psi_0$ according to the equations 1 and 5, it follows that:

$$a_w = a_{w0} V_0/V \quad [7].$$

By replacing V of equation 6 in equation 7, it follows that equation 8, which represents the water activity as a function of the length of the water blade (L) contained in the plates.

$$a_w = a_{w0}^{(L0/L)2} \quad [8].$$

Similarly, by replacing V of equation 6 in equation 5, it follows that:

$$\Psi_s = -nRT/(0.005L^2 tg\alpha) \quad [9].$$

Thus, if the osmotic potential varies between $\Psi_{s0}$ and $\Psi_s$, then according to equation 7 it follows that:

$$\Psi_s = \Psi_{s0}(L0/L)^2 = \Psi_{s0}(C_0/C)^2 \quad [10].$$

wherein C is the concentration of the solution between the plates at a given moment.

The total water potential, considering also the tension with which water is retained between the plates, can be then obtained, by adding equation 4 to equation 10.

$$\Psi_w = \Psi_{s0}(C_0/C)^2 - 2\sigma/[L \; tg(\alpha)] \quad [11];$$

Figure 11:
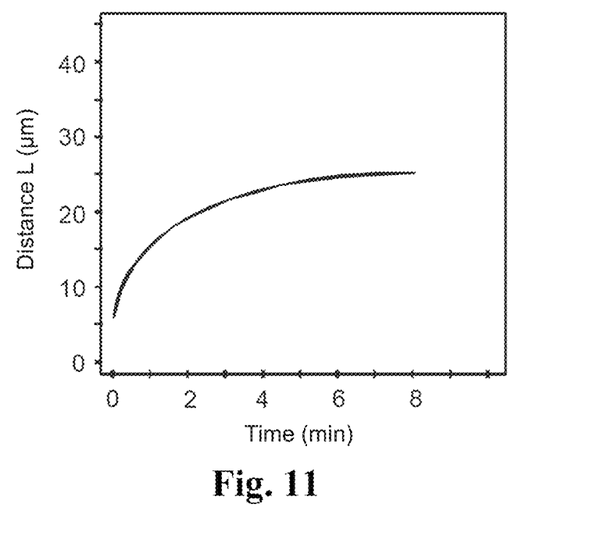
FIG. 11 illustrates the response of water potential balance for a dihedron sensor with a 20 μm at the edge pressed against the surface of a carrot root surface.

The total balance time in the measurement of water potential (FIG. 11) depends much on the thermal balance between the edge and the sample, but, as mentioned before, it may also depend on the absorption of water on the outer surfaces of the sensor. Ideally, without adsorption in the outer surfaces, dynamic thermal balances with differences in temperature between the sample surface and the edge surface of the dihedral sensor with difference on the order of (□0.001° C.) can be obtained in minutes, if the distance between the sample and the dihedral sensor is shorter than 30 μm, within the indicative geometry illustrated in FIG. 3.

An important feature which should be kept in mind when using the equations 10 and 11 to measure $\Psi_w$ and $\Psi_S$ is that most of the volume of the solution added to the sensor is evaporated in few seconds after application. In this way, the value of L0 should be estimated in accordance with the dihedron ($\alpha$), as shown in Table 1.

In theory, equations 10 and 11, considered for measuring water activity, could also be used for measuring the activity of other volatile substances, which, as ethanol, for example, have affinity, and wet the inner surfaces of the sensor.

Response and Assessments in Water Activity and Potential

Figure 8:
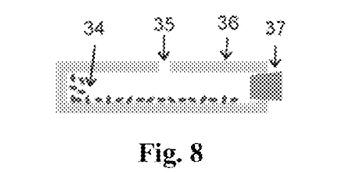
FIG. 8 shows a system with orifice and hydrophilic substances in a solid medium for assessing measurements of water activity and relative humidity with a dihedron sensor.

FIG. 8 illustrates a system with a bore (35) and hydrophilic substrates of solid particles (34) impregnated with hygroscopic substance of known water activity, with which one makes gauges the measurements of water activity and relative humidity carried out with the dihedral sensor. Therefore, the calibration assembly is a box (36) with cover (37), containing a hydrophilic substrate with known water activity (34) and a bore (35) in which the dihedron edge (3) is set to enable hygroscopic balance required for gauging water activity or water potential. This is a durable and robust type of calibrator. The flexibility of this gauger results from the range of available substances for obtaining atmospheres with reference water activity (Windyon & Hates, Ecology, v. 41, p. 232-237, 1060).

Figure 10:
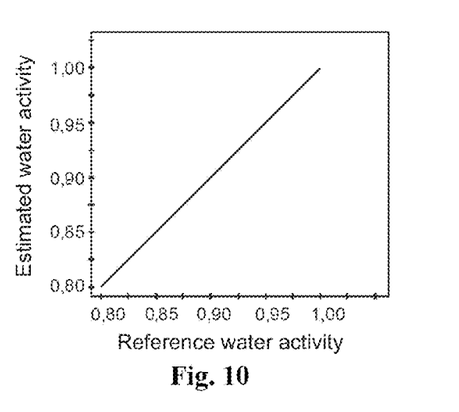
FIG. 10 shows a curve of water activity of reference and water activity calculated with the dihedron sensor, the measurement being carried out with the aid of an NaCl solution.

By using this saline solution (as NaCl) as described (eq. 8 and eq. 10), one can carry out measurements in a wide range of water activity, as shown in FIG. 10. This type of measurement is important for use on processed foods like sweets, for example.

In measurements of water activity and water potential with the dihedral sensor, with or without the use of a solution between the plates, an important feature is the balance time. In assays for determining the water potential in plant matter like carrot roots, the typical response of the sensor in time is of the type illustrated in FIG. 11. These response times are proportional to the volumes of water exchanged per unit of length of the sensor and proportional to the square of the distance between the edge (3) of the dihedral sensor and the surface of the plant organ (11). The hydraulic conductivity and internal gradients of water potential existing in the product at the beginning of the measurement may be cause of additional delay in measurements of water potential or water activity.

Figure 12:
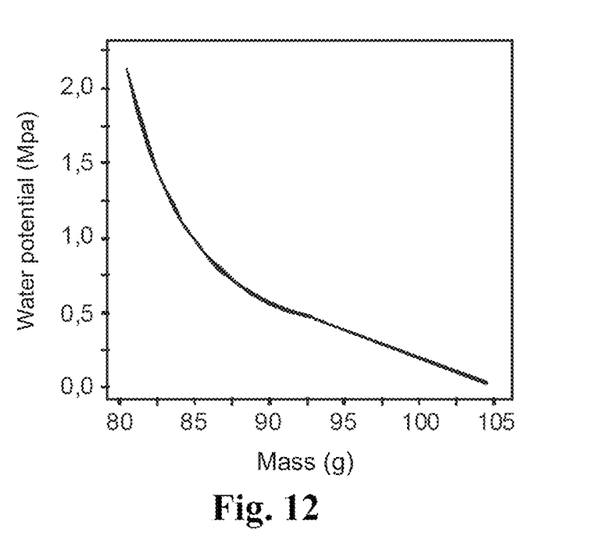
FIG. 12 illustrates the mass of carrot root and water potential measured with the dihedron sensor.

In studies of water potential, which can be effected without using saline solution between the dihedron plates, expected results of water potential measured as a function of water loss for products like carrot roots are of the type illustrated in FIG. 12.

Additional Limitations and Potentialities

Imperfections in the of the dihedral sensor are a problem and, at the same time, a need so that water can flow and the instrument can function. If the plates were perfect, as the analogy of the name dihedron suggests, the dihedral sensor would simply not function, because this edge would be perfectly impermeable to passage of liquid or gases. Thus, roughness and smoothness of the plates used should be conformed to the applications aimed at. Thus, flattened ordinary glass plates and porous element plates of critical tension higher than 2.0 MPa are suitable for most applications of water tension in soils. Materials of greater perfection and smoothness, however, are required for higher measurements of water potential and water tensions up to the order of 3.0 MPa, when the surface imperfections already should be lower than 100 nm.

Dihedral sensor with hydrophilic outer surface may constitute a possible problem for at least two reasons: first, the hydrophilic surface is a place for deposition of layers of water molecules, which may delay the balance in measurements of water potential, just as it occurs in other systems; Secondly, since the outer surfaces are hydrophilic, they may be drains, or outlet paths for water or the solution contained in the dihedron. This is a problem in the particular case of there being solutions in the dihedron, since the solution placed, for example, for monitoring water activity in air may migrate onto the outer surfaces of the sensor. As a result, for specific applications in which these phenomena may not take place, the outer dihedron faces require a coating with hydrophobic molecules, which prevent adsorption and surface escape of polar solutions.

Unlike the systems of dew-point hygrometry by surface cooling, the system of the present invention is little prone to impregnation of its surfaces by impurities from the air. This occurs because air gets into the dihedron mainly by diffusion, which reduces the velocity of contamination with impurities. This problem is particularly smaller in dihedral sensors with hermetic closing of the sides. In all embodiments, however, there may be contaminations due movements of contaminated water and by volatile organic impurities.

A second feature is that the temperature of the edge surface can be adjusted by Peltier effect and measured by using thermocouples, as used in tunneling microscopy. These improvements can be obtained by deposition of the adequate metals onto the glass surface. Thus, one adds to the qualities of the present technique the possibility of measuring lower water activities or simply producing initial condensation of water for operation of the system in monitoring water activity.

If the system is hermetic and the meniscus position is kept in a reference position thanks to the application of gas pressure, then the method will be one of isopiestic balance, that is, with constant weight in the sense that in the balance the water mass contained in the dihedron remains unchanged during the measurements. The isopiestic condition enables one to monitor the water potential more rapidly and with less influence on the water potential of small biological samples that are more sensitive to the variations of the absolute amount of water.

The invention claimed is:

1. A sensor for evaluating at least one of a tension, potential or activity of a liquid of a sample, comprising:
    two plates,
        wherein the two plates comprise an upper plate and a lower plate,
        the upper plate and the lower plate being statically disposed to each other such as to form a dihedral structure, the dihedral structure having a fixed dihedral angle ($\alpha$) between the upper plate and the lower plate,
    the sensor further comprising,
    an edge of the two plates located at a vertex end of the two plates,
    a junction between the two plates defining an opening extending from the edge to an internal space cooperatively defined between the two plates, and
    a position of a meniscus of the liquid being readable via the upper plate,
    wherein the sensor is configured to have a single and permanent magnitude for the fixed dihedral angle ($\alpha$) for reading the position of the meniscus of the liquid at an orthogonal distance from the edge, after the position of the meniscus achieves balance, and for calculating, on the basis of the orthogonal distance, at least one of the tension, potential or activity of the liquid of the sample.

2. The sensor according to claim 1, further comprising a porous element coupled to the edge of the two plates for providing direct contact with the sample.

3. The sensor according to claim 2, wherein the porous element is elongate, and
    the elongate porous element is provided with side walls that are impermeable in a proximal portion of the elongate porous element and permeable in a distal portion of the elongate porous element.

4. The sensor according to claim 1, further comprising at least one vent bore in the upper plate or in the lower plate in a distance from the edge corresponding to one specific liquid tension for direct measurements of liquid tensions by air-flow or gas-flow induced passage through the vent bore.

5. A sensor for evaluating at least one of a tension, potential or activity of a liquid of a sample, comprising:
    two plates,
        wherein the two plates comprise an upper plate and lower plate,
        the upper plate and the lower plate are secured relative to each other at a fixed dihedral angle ($\alpha$),
    an edge of the two plates is located at a vertex end of the two plates,
    a junction between the two plates defines an opening extending from the edge to an internal space cooperatively defined between the two plates,
    said internal space between the two plates being hermetically closed, except from the opening extending from the edge to the internal space, and
    further comprising an opening in a region opposite the edge, through which the internal space of the sensor communicates with a pressure modulator provided with a manometer.

6. The sensor according to claim 1,
    wherein one or both of the two plates comprises a chamfer at the vertex end thereof, the chamfer defining a concave microchamber (12) providing means of indirect communication of the sample with the opening.

7. A process for measuring at least one of a tension, potential or activity of a liquid of a sample by means of a sensor that comprises an upper plate and a lower plate, the plates arranged relative to each other forming a fixed dihedral angle ($\alpha$), the process comprising the following steps:
    forming a dihedral structure by statically disposing the upper plate and the lower plate to each other, wherein the dihedral structure defines the fixed dihedral angle ($\alpha$) which assumes a single and permanent magnitude while the sensor is used for evaluating at least one of a tension, potential or activity of a liquid sample,
    establishing direct or indirect contact between an edge of the sensor and the sample, the edge located at a vertex end of the upper plate and the lower plate,
    reading the position of a meniscus at an orthogonal distance from the edge, after the position of the meniscus achieves balance; and
    calculating, on the basis of the orthogonal distance, at least one of the tension, potential or activity of the liquid of the sample.

8. The process according to claim 7, further comprising: enabling, with application of a known volume of a solution of known concentration, measuring water activity more reduced than one manages to measure by employing pure water between the sensor plates, through variations of the orthogonal distance.

9. The process according to claim 7, further comprising enabling measurement of tension in liquids having affinity for a surface of one or both of the two plates that define the internal space.

10. The process according to claim 7, further comprising enabling measurement of the activity of volatile liquids having affinity for a surface of one or both of the two plates that define the internal space.

11. The process according to claim 7, wherein the internal space between the two plates of the sensor is hermetically closed, except for leaving open the opening that extends from the edge to the internal space,
    the process further comprising enabling isopiestic operation by maintaining the meniscus position fixed by pneumatic variation of the internal pressure of the internal space, for measuring tension and potential at constant volume and also in gauging orthogonal distance versus applied pressure.

12. The process according to claim 8, wherein the solution of known concentration is NaCl solution.

13. The sensor according to claim 1, wherein the upper plate is transparent.

14. The sensor according to claim 5, wherein one or both of the two plates comprises a chamfer at the vertex end thereof, the chamfer defining a concave microchamber in providing means of indirect communication of the sample with the opening.

* * * * *